United States Patent
Mertens et al.

(10) Patent No.: US 7,285,599 B2
(45) Date of Patent: Oct. 23, 2007

(54) PULVERULENT, CROSS-LINKED POLYMERS CAPABLE OF ABSORBING AQUEOUS LIQUIDS

(75) Inventors: Richard Mertens, Krefeld (DE); Harren Jörg, Krefeld (DE)

(73) Assignee: Stockhausen GmbH, Krefeld (DE)

( * ) Notice: Subject to any disclaimer, the term of this patent is extended or adjusted under 35 U.S.C. 154(b) by 0 days.

(21) Appl. No.: 10/379,827

(22) Filed: Mar. 4, 2003

(65) Prior Publication Data

US 2004/0176544 A1    Sep. 9, 2004

Related U.S. Application Data

(63) Continuation of application No. PCT/EP01/06375, filed on Jun. 5, 2001.

(30) Foreign Application Priority Data

Sep. 4, 2000    (DE) ................. 100 43 710

(51) Int. Cl.
*C08F 220/06* (2006.01)
(52) U.S. Cl. .................... 525/360; 525/55
(58) Field of Classification Search ........... 525/360, 525/55
See application file for complete search history.

(56) References Cited

U.S. PATENT DOCUMENTS

| | | | |
|---|---|---|---|
| 4,043,952 A | | 8/1977 | Ganslaw et al. |
| 4,076,663 A | | 2/1978 | Masuda et al. |
| 4,286,082 A | | 8/1981 | Tsubakimoto et al. |
| 4,340,706 A | | 7/1982 | Obayashi et al. |
| 4,640,810 A | | 2/1987 | Laursen et al. |
| 5,669,894 A | | 9/1997 | Goldman et al. |
| 5,837,789 A | * | 11/1998 | Stockhausen et al. ....... 526/320 |
| 5,849,405 A | * | 12/1998 | Wang et al. ............. 428/304.4 |
| 6,388,000 B1 | * | 5/2002 | Irie et al. ................ 524/556 |
| 6,831,142 B2 | | 12/2004 | Mertens et al. |

FOREIGN PATENT DOCUMENTS

| | | |
|---|---|---|
| DE | 27 06 135 A1 | 2/1977 |
| DE | 28 40 010 A1 | 9/1978 |
| DE | 35 03 458 A1 | 2/1985 |
| DE | 37 13 601 A1 | 4/1987 |
| DE | 40 20 780 C1 | 6/1990 |
| DE | 43 33 056 A1 | 9/1993 |
| DE | 44 18 319 A1 | 5/1994 |
| DE | 44 18 818 A1 | 5/1994 |
| DE | 195 05 709 A1 | 2/1995 |
| DE | 196 46 484 A1 | 11/1996 |
| DE | 197 50 890 A1 | 11/1997 |
| EP | 0 233 067 A2 | 8/1987 |
| EP | 0 574 260 A1 | 12/1993 |
| EP | 0 889 063 A1 | 1/1998 |
| EP | 0 850 615 A1 | 7/1998 |
| JP | 9-124879 | 5/1997 |
| JP | 09124879 A * | 5/1997 |
| WO | WO 95/22356 | 8/1995 |
| WO | WO 96/05234 | 2/1996 |
| WO | WO 97/12575 | 4/1997 |
| WO | WO 98/48857 | 11/1998 |
| WO | WO 98/49221 | 11/1998 |
| WO | WO 9849221 A1 * | 11/1998 |
| WO | WO 99/49905 | 10/1999 |
| WO | WO 00/53664 | 9/2000 |

OTHER PUBLICATIONS

Translation to JP 09124879 (1997).*

* cited by examiner

*Primary Examiner*—Kelechi C. Egwim
(74) *Attorney, Agent, or Firm*—Smith Moore LLP

(57) ABSTRACT

The invention relates to absorbent, cross-linked polymers based on partially neutralized, monoethylenically unsaturated monomers that bear acidic groups. Said polymers exhibit improved properties with regard to their ability to transport liquids in a swollen state. The surface of the polymers is postreticulated, using a combination of an organic cross-linking compound, excluding polyols, and a cation that is in salt form in an aqueous solution.

22 Claims, No Drawings

PULVERULENT, CROSS-LINKED POLYMERS CAPABLE OF ABSORBING AQUEOUS LIQUIDS

This application is a continuation of International Application No. PCT/EP01/06375, internationally filed Jun. 5, 2001.

FIELD OF THE INVENTION

The invention relates to pulverulent, cross-linked polymers (superabsorbers) which absorb water, aqueous liquids as well as blood, having improved properties, in particular having improved retention and improved retaining capability for liquids at pressure, and improved ability to transport liquids, the preparation thereof and the use thereof as absorbents in hygiene articles and in technical sectors.

BACKGROUND OF THE INVENTION

Superabsorbers are water-insoluble, cross-linked polymers which, with swelling and the formation of hydrogels, are able to absorb, and retain at a certain pressure, large quantities of aqueous liquids and body fluids such as, for example, urine or blood. As a result of these characteristic properties these polymers are incorporated in sanitary articles such as, for example, babies' nappies, incontinence products or sanitary towels, by way of a principal application.

The superabsorbers which are currently available commercially are substantially cross-linked polyacrylic acids or cross-linked starch-acrylic acid graft polymers, in which some of the carboxyl groups are neutralised with caustic soda or caustic potash solution.

The increasing tendency towards increasingly small, thin sanitary articles such as babies' nappies, incontinence products and sanitary towels arises from aesthetic and environmental considerations. In order to guarantee that the total retention capacity of the sanitary articles remains unchanged, this requirement can be met only by reducing the proportion of bulky fluff. As a result, the superabsorber is required to serve further functions in terms of transportation and distribution of liquid, which can be summarized as permeability properties.

In the case of superabsorber materials permeability is understood to mean the ability, in the swollen state, to transport liquids which have been added and to distribute them three-dimensionally. This process takes place in the swollen superabsorber gel by way of capillary transportation through interstices between the gel particles. Transportation of liquid through swollen superabsorber particles themselves is subject to the laws of diffusion and is a very slow process which plays no part in the distribution of liquid in the situation in which the sanitary article is used. In the case of superabsorber materials which owing to inadequate gel stability cannot bring about capillary transportation, a separation of the particles from one another was ensured by embedding these materials in a fiber matrix, avoiding the phenomenon of gel blocking. In new-generation nappy constructions the absorber layer contains only little fiber material, or none at all, to support the transportation of liquid. The superabsorbers used here must accordingly be sufficiently stable in the swollen state for the swollen gel still to have an adequate quantity of capillary spaces through which liquid can be transported.

In order to obtain superabsorber materials having high gel strength, the degree of cross-linking of the polymer can, on the one hand, be increased, which necessarily results in a reduction in swelling ability and retention capacity. An optimized combination of different cross-linking agents and comonomers, such as is described in Patent Specification DE 196 46 484, was admittedly able to improve the permeability properties, but not to a level which, for example, enables a layer which optionally comprises only superabsorbers to be built into in a nappy construction.

Methods of post-cross-linking the surface of the polymer particles can furthermore be used. In so-called post-cross-linking the carboxyl groups of the polymer molecules on the surface of the superabsorber particles are reacted with different post-cross-linking agents which are capable of reacting with at least two of the carboxyl groups close to the surface. As well as bringing about increased gel strength, the ability to absorb liquid at pressure is in particular greatly improved because the known phenomenon of gel blocking, in which polymer particles which have begun to stick together, thus preventing further liquid absorption is suppressed.

The surface treatment of liquid-absorbent resins is already known. Ionic complexing of the carboxyl groups close to the surface with polyvalent metal cations is proposed in U.S. Pat. No. 4,043,952 in order to improve dispersibility. The treatment takes place with salts of polyvalent metals which are dispersed in organic, optionally water-containing, solvents (alcohols and other organic solvents).

DE-A-40 20 780 describes a post-treatment of superabsorber polymers with reactive, surface-cross-linking compounds (alkylene carbonates) in order to increase the liquid absorption capability at pressure. DE-A-35 03 458 describes a surface post-cross-linking of superabsorbent polymers with polyfunctional cross-linking agents such as polyvalent metal compounds in the presence of inert, inorganic powder such as $SiO_2$ in order to improve the absorption properties and create a non-adherent gel of the polymer particles.

According to the teaching of EP-A-0 574 260 superabsorbent polymers are obtained which have a low residual monomer content which does not change crucially even when surface cross-linking takes place, if certain conditions are observed in the polymerisation and the post-cross-linking is carried out with conventional polyfunctional cross-linking agents such as polyols, alkylene carbonates, polyvalent metal salts under conventional conditions. The post-cross-linked polymers show good absorption without the application of pressure.

According to EP-A-0 889 063 superabsorbent polymers which are preferably already surface-cross-linked can be equipped to resist radical degradation by body fluids, in particular L-ascorbic acid by post-treatment with a titanium or zirconium compound and a compound which chelates these metal compounds.

EP 0 233 067 describes water-absorbent resins which are cross-linked on the surface, which are obtained by the reaction of a superabsorbent polymer powder having from 1 to 40 wt. % of an aluminium compound, in relation to the polymer powder. A mixture of water and diols is used as the treatment solution, which should render the use of low alcohols as solvents superfluous. 100 parts by weight of cross-linking agent solution are preferably applied to from 100 to 300 parts by weight of absorber. The diols (for example polyethylene glycol 400 and 2000, 1,3-butanediol or 1,5-pentanediol) which are added to the reaction medium, water, also serve, inter alia, to prevent agglomeration of the superabsorber when treated with the large quantities of aqueous treatment solution which are used here. The solvent is removed in subsequent drying at 100° C. The properties of the polymers thus treated are inadequate, with no improvement in the absorbency at pressure being achieved. A treatment with large quantities of treatment solution is furthermore not economically practicable in modem continuous processes.

WO 96/05234 describes a process for the treatment of superabsorbent polymers, according to which the surface of the absorber particles, which contain at least 10 wt. % water, was equipped with a cross-linked layer obtained by a reaction of a reactive hydrophilic polymer or a reactive organometallic compound with an at least difunctional cross-linking agent at temperatures below 100° C. Metal salts are not listed. The metal compounds utilised must be capable of reacting with the functional groups of the cross-linking agent. Organometallic compounds which should be present in a ratio by weight of from 0.1 to 30 in relation to the cross-linking compound are therefore recommended as the metal compounds. The polymers obtained should have a balanced ratio of absorption, gel strength and permeability, with the measured values which are indicated being obtained under less critical conditions. Thus, for example, the absorption and the permeability are determined with no pressure load. A disadvantage of this known process is the use of solvents and toxicologically risky cross-linking reagents such as, for example, the polyimines, alkoxylated silane and titanium compounds and epoxides, which are cited as preferred.

According to the teaching of WO 95/22356 and WO 97/12575 an improvement in the permeability properties and liquid transportation properties is obtained by a corresponding treatment of commercially obtainable superabsorber polymers with amino polymers in organic solvents. The serious disadvantage of the process described here, apart from the use of toxicologically risky polyamines and poly-imines, lies in the use of large quantities of organic solvents which are necessary for the treatment of the polymers. The issue of safety and the cost associated with this preclude large-scale industrial production. Apart from the toxicological risk posed by these treatment agents, consideration should furthermore be given to their additional tendency to decompose at the high post-cross-linking temperatures, which is manifested, inter alia, in a yellow coloration of the absorber particles.

In order to prepare water-absorbent polymers having better abrasion resistance, Japanese published patent application JP-A-09124879 teaches surface post-cross-linking with polyfunctional cross-linking agents, in which the water content of the polymer particles following surface cross-linking is readjusted to from 3 to 9 wt. %, and this quantity of water may contain inorganic compounds such as metal salts.

Superabsorbent polymers which are contacted in particle form with polyvalent metal salts by dry mixing and are then provided with a specific quantity of a liquid binder such as water or polyols according to WO 98/48857, should have improved gel blocking when absorbing aqueous liquids. The polymer particles may undergo a surface post-cross-linking before this treatment.

In order to minimise the tendency of superabsorbent, post-cross-linked polymer particles to agglomerate as a result of electrostatic charging, WO 98/49221 recommends re-moistening the polymer particles with an aqueous additive solution up to 10 wt. % water. These aqueous solutions may contain monovalent or polyvalent ions or propoxylated polyols. It is also possible to contact the polymer particles with the aqueous additive solution as early as before the surface post-treatment, as a result of which a more uniform distribution of the surface treatment agents should be achieved.

No reference to any possibility, in the post-cross-linking stage, of also dramatically increasing permeability properties, while preserving a high retention capacity and absorption capability for liquid at pressure, is apparent in the prior art described hereinabove.

SUMMARY OF THE INVENTION

The object of the present invention was therefore to provide superabsorbent polymers which have an improved combination of properties, in which in particular not only a high absorption capacity at pressure, but also the normally opposing properties of high retention capacity and good permeability are combined, that is to say, a level of the combination of properties, at which apart from a retention value of at least 25 g/g, an SFC value of at least $45 \cdot 10^{-7}$, preferably of at least $50 \cdot 10^{-7}$ cm$^3$ sec/g is present. In particular, the object is to provide superabsorbent polymers which above all are suitable for use in very thin nappy constructions containing a very high proportion of superabsorbers. Polymers having retention values of at least 25 g/g and permeability values of SFC>at least $70 \cdot 10^{-7}$ cm$^3$ sec/g are preferred.

A further object of the invention was to find processes for the preparation of such superabsorbent polymers, which are simple, economical and safe to carry out, which deliver a uniform product quality and in which in particular low solvent quantities are used and organic solvents are as far as possible avoided. Furthermore, the processes should be able to be carried out without the use of toxicologically risky substances.

The object according to the invention is achieved by the provision of a pulverulent polymer which absorbs water, aqueous or serous liquids as well as blood, which is post-cross-linked on the surface and is synthesised from a) from 55 to 99.9 wt. % polymerised, ethylenically unsaturated, acid group-containing monomers which are at least 25 mol % neutralised.

b) from 0 to 40 wt. % polymerised, ethylenically unsaturated monomers which are copolymerisable with a), c) from 0.1 to 5.0 wt. % of one or more polymerised cross-linking agents, d) from 0 to 30 wt. % of a water-soluble polymer, wherein the sum of the quantities by weight a) to d) is 100 wt. %, wherein the polymer is coated and post-cross-linked, with heating, with e) from 0.01 to 5 wt. %, in relation to the polymer, of an organic surface post-cross-linking agent, with the exception of polyols, in the form of an aqueous solution and with f) from 0.001 to 1.0 wt. %, in relation to the polymer, of a cation in the form of a salt dissolved in an aqueous solution, wherein the total quantity of water of the coating solution is from 0.5 to 10 wt. %, in relation to the polymer, and the ratio by weight of the salt to the post-cross-linking agent is within the range 1:0.8 to 1:4, and wherein cross-linked polyacrylic acids which are up to 70 mol % present as Na salts and which have been surface post-cross-linked with an aqueous solution containing $Al_2(SO_4)_3 \cdot 18H_2O$ and 1,3-dioxolan-2-one in a ratio by weight of from 1:2 or 1:2.5 or 1:3.33 or 1:1.666 or 1:1.142 or 1:1 or with $Al_2(SO_4)_3 \cdot 14H_2O$ and 1,3-dioxolan-2-one in a ratio by weight of 1:2 or with $Al_2(SO_4)_3 \cdot 18H_2O$ and ethylene glycol diglycidyl ether in a ratio by weight of 1:1 or with aluminium chloride.$6H_2O$ and 1,3-dioxolan-2-one in a ratio by weight of 1:1.43 or with iron(III) chloride.$6H_2O$ and 1,3-dioxolan-2-one in a ratio by weight of 1:1.43 or Ca acetate.hydrate or Mg acetate.hydrate and 1,3-dioxolan-2-one in a ratio by weight of 1:10, or cross-linked polyacrylic acid which is 70 mol % present as Na salt, and which is grafted on native waxy maize starch or polyvinyl alcohol and has been coated and surface post-cross-linked with an aqueous solution containing $Al_2(SO_4)_3 \cdot 14H_2O$ and 1,3-dioxolan-2-one in a ratio by weight of 1:2, are excepted.

DETAILED DESCRIPTION OF THE INVENTION

Surprisingly, in fact, as a result of the coating of a particulate absorbent polymer with an aqueous solution of an organic cross-linking agent with the exception of polyols which has reacted with the molecule groups close to the surface, preferably with the carboxyl groups, in the presence of a cation of a salt component, preferably with heating to from at least 150 to 250° C., a superabsorbent polymer results having significantly improved permeability properties, with very good retention capacity.

Totally unexpectedly, the aqueous solution of the combination according to the invention of post-cross-linking components leads to the desired outcome, namely superabsorber resins having a high retention capacity even at pressure with simultaneously excellent permeability properties. A sequential, separate use both of an aqueous solution of the organic post-cross-linking agent and of the aqueous salt solution, with heating in each case, does not lead to a comparably good product characteristic.

The sole use of organic post-cross-linking agents such as, for example, alkylene carbonates in aqueous solution, or the combination of organic post-cross-linking agents leads to products having a high retention capacity, high gel strength and high absorption capability at pressure. A significant increase in the permeability in the swollen state can, however, be achieved only by a correspondingly higher degree of cross-linking of the polymers in the polymerisation, or a stronger post-cross-linking (increased quantities of post-cross-linking agent or more drastic conditions) and the associated loss of retention capacity.

The sole post-cross-linking with cations of high positive charge density likewise does not lead to polymers having the desired combination of properties. In particular, satisfactory values for liquid absorption at pressure cannot be obtained, nor good permeability properties. No improvement in the stability at pressure nor, above and beyond this, of the liquid transporting properties in the swollen state is achieved. Nor can the required properties be obtained by small quantities of organic post-cross-linking agents and large quantities of cations.

According to the invention, organic at least bifunctional compounds with the exception of polyols are preferably utilised as the organic post-cross-linking component e) of claim 1, which react with the COOH groups of the polymer which are close to the surface. These are, for example, alkylene carbonates, preferably having $C_4$-$C_{10}$, particularly preferably having $C_4$-$C_6$ in the ring, such as 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one or 1,3-dioxepan-1-one, 1,3-dioxolans, 1,3-dioxanes, with 1,3-dioxolan-2-one or 4-methyl-1,3-dioxolan-2-one being preferred.

The following may additionally be utilized as the post-cross-linking component e) of claim 1:

amino alcohols, preferably aliphatic amino alcohols, preferably having $C_2$-$C_{10}$ such as, for example, diethanolamine, triethanolamine. Further suitable organic post-cross-linking compounds which should, however, be seen as critical on account of their toxicological potential are: polyepoxides such as polyepoxide ethers or esters of polyfunctional, preferably difunctional, polyols or carboxylic acids, for example ethylene glycol diglycidyl ether, polyethylene glycol diglycidyl ether, glycerol polyglycidyl ether, polyglycerol polyglycidyl ether, propylene glycol diglycidyl ether, polypropylene glycol diglycidyl ether, neopentyl glycol diglycidyl ether, pentaerythritol polyglycidyl ether, hexanediol diglycidyl ether, trimethylolpropane polyglycidyl ether, sorbitol polyglycidyl ether, phthalic acid diglycidyl ester, adipic acid diglycidyl ester, 1,4-phenylene-bis(2-oxazoline), glycidol; polyisocyanates, preferably diisocyanates such as, for example, 2,4-toluene diisocyanate and hexamethylene diisocyanate; halo epoxides such as, for example, epichlorohydrin and epibromohydrin and α-methyl epichlorohydrin, aliphatic polyamine compounds such as, for example, ethylenediamine, diethylenetriamine, triethylenetetramine, polyallylamine or polyethylene imine. Polyoxazoline compounds such as, for example 1,2-ethylene bisoxazoline as well as oxazolidinones such as, for example, N-acyl-2-oxazolidinones as well as 2-oxo-tetrahydro-1,3-oxazines are furthermore utilisable as post-cross-linking compounds. The organic post-cross-linking component or mixtures thereof is/are utilised in quantities of from 0.01 to 5 wt. %, preferably 0.1-2.5 wt. % and particularly preferably 0.5 to 1.5 wt. %, in relation to the polymer which is to be cross-linked on its surface.

Of the organic post-cross-linking components named above, the alkylene carbonates are preferably utilized.

According to the invention, aqueous solutions of water-soluble salts are preferably utilized as the component f) of claim 1 to cross-link the carboxylate groups close to the surface, which have as anions chlorides, bromides, sulfates, carbonates, nitrates, phosphates or organic anions such as acetates and lactates. The cations are monovalent and polyvalent cations which are derived from alkali metals such as potassium, sodium, lithium, preferably lithium. Divalent cations used according to the invention are derived from zinc, beryllium, alkaline earth metals such as magnesium, calcium, strontium, with magnesium being preferred. Further examples of trivalent and higher-valent cations which are preferably utilized according to the invention are cations of aluminium, iron, chromium, manganese, titanium, zirconium and other transition metals as well as double salts of such cations or mixtures of the named salts. Trivalent and higher-valent cations and, of these, in particular aluminium salts and alums and various hydrates thereof such as, for example, $AlCl_3 \times 6\ H_2O$, $NaAl(SO_4)_2 \times 12\ H_2O$, $KAl(SO)_4 \times 12\ H_2O$ or $Al_2(SO_4)_3 \times 14-18\ H_2O$ or $Al(NO_3)_3 \times 9\ H_2O$ are preferably utilised. $Al2(SO_4)_3$ or $Al(NO_3)_3$ and hydrates thereof are preferably used. The salt component, calculated on the cation, is utilised in quantities of from 0.001 to 1.0 wt. %, preferably 0.005-0.5 wt. % and more preferably 0.01 to 0.2 wt. %, in relation to the polymer. The preferred ratio by weight of water-soluble salt to post-cross-linking agent is from 1:1 to 1:3.5, and more preferably 1:1.2 to 1:2.5.

A combination of trivalent cations, preferably $Al^{3+}$ in combination with alkylene carbonates, preferably 1,3-dioxolan-2-one, is more preferably utilized.

The water-absorbing polymer which is cross-linked on the surface is obtained by polymerisation of a) from 55 to 99.9 wt. % of a monomer having single unsaturation, with acid groups. Here, carboxyl group-containing monomers are preferred such as, for example, acrylic acid, methacrylic acid or 2-acrylamido-2-methylpropane sulfonic acid or mixtures of these monomers. It is preferred that at least 50 wt. % and preferably at least 75 wt. % of the acid groups are carboxyl groups. The acid groups are at least 25 mol % neutralised, that is to say they are present as sodium, potassium or ammonium salts. The degree of neutralisation is preferably around at least 50 mol %. A polymer which has been obtained by polymerisation of acrylic acid or methacrylic acid, whereof the carboxyl groups are from 50 to 80 mol % neutralised, in the presence of cross-linking agents is preferred.

From 0 to 40 wt. % ethylenically unsaturated monomers which are copolymerisable with a), such as, for example, acrylamide, methacrylamine, hydroxyethyl acrylate, dimethylaminoalkyl (meth)acrylate, dimethylaminopropyl acrylamide or acrylamidopropyl trimethylammonium chloride may be used as further monomers b) for the preparation of the absorbent polymers. A proportion greater than 40 wt. % of these monomers may impair the swelling capacity of the polymers.

All compounds which carry at least two ethylenically unsaturated double bonds or one ethylenically unsaturated double bond and a functional group which is reactive to acid groups of the monomers a) or a plurality of functional groups which are reactive to acid groups may be used as the cross-linking component c) which is present during the polymerisation of a) and b). The following might be named as examples: aliphatic amides such as, for example, methylene bisacrylamide or methylene bismethacrylamide or ethylene bisacrylamide, furthermore aliphatic esters of polyols or alkoxylated polyols with ethylenically unsaturated acids, such as di(meth)acrylates or tri(meth)acrylates, butanediol or ethylene glycol, polyglycols, trimethylolpropane, di- and triacrylic esters of trimethylolpropane which is preferably alkoxylated with from 1 to 30 mole alkylene oxide, preferably ethoxylated trimethylolpropane, acrylic and methacrylic esters of glycerol and pentaerythritol, as well as of glycerol and pentaerythritol which have been ethoxylated preferably with from 1 to 30 mole ethylene oxide, furthermore allyl compounds such as allyl (meth)acrylate, alkoxylated allyl (meth)acrylate reacted preferably with from 1 to 30 mole ethylene oxide, triallyl cyanurate, triallyl isocyanurate, maleic acid diallyl ester, polyallyl ester, tetraallyloxyethane, triallylamine, tetraallyl ethylenediamine, allyl esters of phosphoric acid or phosphorous acid, furthermore cross-linkable monomers such as N-methylol compounds of unsaturated amides such as of methacrylamide or acrylamide and the ethers derived therefrom. Mixtures of the cross-linking agents named may likewise be utilized. The cross-linking comonomer content is around 0.1 to 5 wt. %, preferably around 0.01 to 3.0 wt. %, in relation to the total quantity of monomers.

As the water-soluble polymers d) from 0-30 wt. % water-soluble polymers, such as partially or completely saponified polyvinyl acetates, polyvinyl pyrrolidone, starch or starch derivatives, polyglycols or polyacrylic acids may be contained, preferably polymerised into, the absorbent polymers according to the invention. The molecular weight of these polymers is not critical provided that they are water-soluble. Preferred water-soluble polymers are starch and polyvinyl alcohol. The preferred content of such water-soluble polymers in the absorbent polymer according to the invention is around 0 to 30 wt. %, preferably 0 to 5 wt. %, in relation to the total quantity of the components a) to d). The water-soluble polymers, preferably synthetic polymers such as polyvinyl alcohol, may also serve as a graft backbone for the monomers which are to be polymerized.

The usual initiators such as, for example, azo or peroxo compounds, redox systems or UV initiators (sensitisers) are used to initiate the radical polymerisation.

The polymers according to the invention are preferably prepared in accordance with two methods:

In accordance with the first method the partially neutralised monomer a), preferably acrylic acid in aqueous solution, is converted by radical polymerisation in the presence of cross-linking agents and optionally further components into a gel which is comminuted, dried, ground and screened to the desired particle size. This solution polymerisation may be carried out in continuous or discontinuous manner. The prior art exhibits a broad spectrum of possible variations as to the concentration ratios, temperatures, type and quantity of the initiators. Typical processes are described in the following publications: U.S. Pat. No. 4,286,082, DE 27 06 135 and U.S. Pat. No. 4,076,663, whose corresponding disclosure is included here as a reference.

Inverse suspension and emulsion polymerisation may also be used for the preparation of the products according to the invention. According to these processes an aqueous, partially neutralised solution of the monomers a), preferably acrylic acid, is dispersed with the aid of protective colloids and/or emulsifiers in a hydrophobic, organic solvent and the polymerisation is initiated by radical initiators. The cross-linking agents are either dissolved in the monomer solution and are dispensed together with it, or alternatively they are added separately and optionally during the polymerisation. The addition of a water-soluble polymer d) as a graft backbone takes place optionally by way of the monomer solution or by direct introduction in the oil phase. The water is then removed from the mixture in azeotropic manner and the polymer is filtered off and optionally dried. The cross-linking may take place by polymerising-in a polyfunctional cross-linking agent which is dissolved in the monomer solution, and/or by reacting suitable cross-linking agents with functional groups of the polymer during the polymerisation steps. The processes are described, for example, in the publications U.S. Pat. No. 4,340,706, DE 37 13 601, DE 28 40 010 and WO 96/05234, whose corresponding disclosure is included here as a reference.

The polymer gel is dried to a water content of from 0.5-25 wt. %, preferably 1 to 10 wt. %, more preferably 1 to 8 wt. % at temperatures which are normally within the range 100-200° C.

There are no particular restrictions as to the particle form of the absorbent polymer according to the invention. The polymer may be present in the form of spherules which have been obtained by inverse suspension polymerisation, or in the form of particles of irregular form, which originate from drying and pulverisation of the gel mass from the solution polymerisation. The particle size is normally less than 3000 µm, preferably between 20 and 2000 µm, and more preferably between 150 and 850 µm.

The post-cross-linking components according to the invention are applied in the form of their aqueous solutions. Suitable solvents are water and optionally polar, water-miscible organic solvents such as, for example, acetone, methanol, ethanol or 2-propanol or mixtures thereof. The term "aqueous solution" within the meaning of the invention means in relation to the solvent component that other organic solvents may also be contained in addition to the water. The concentration of the post-cross-linking component in the aqueous solvent in each case may fluctuate within broad limits and is within the range 1 to 80 wt. %, preferably within the range 5 to 65 wt. % and most particularly preferably within the range 10 to 40 wt. %. The preferred solvent for the organic post-cross-linking agent or the salt component is water which is used in a quantity of from 0.5 to 10 wt. %, preferably 0.75 to 5 wt. % and particularly preferably 1.0 to 4 wt. %, in relation to the polymer.

Depending on the solubility of the two components e) and f), the solution is heated to from 20 to 100° C., preferably to 20 to 60° C., before application to the polymer. It is likewise possible to dispense-in separately but concurrently a solution of the organic post-cross-linking agent and a solution of the salt component, if a homogeneous distribution of both components on the polymer is guaranteed and the material subsequently undergoes thermal post-treatment. The application to the polymer of a single aqueous solution in which both components are dissolved is preferred.

The post-cross-linking solution should be mixed very well with the polymer particles. Suitable mixing units for the application of the post-cross-linking solution are, for example, Patterson Kelley mixers, DRAIS turbulent-system mixers, Lödige mixers, Ruberg mixers, screw mixers, pan mixers and fluidised-bed mixers as well as continuously operating vertical mixers in which the polymer powder is mixed by means of blades rotating at high frequency (Schugl mixers). It is also possible to effect the coating of the polymer in a process step during the preparation of the polymer. The process of inverse suspension polymerisation is particularly suitable for this purpose.

After the post-cross-linking solution has been mixed with the polymer particles the post-cross-linking reaction takes place preferably at temperatures within the range>150° C. to 250° C., preferably 160° C. to 220° C. and more preferably 170° C. to 200° C. optimal duration of post-heating can be readily determined by carrying out a small number of experiments in respect of the individual cross-linking agent types. It is limited by the desired property profile of the superabsorber being destroyed again as a result of heat damage. The thermal treatment can be carried out in conventional dryers or ovens; rotary kilns, fluidised bed dryers, disk dryers, paddle dryers or infrared dryers might be named as examples.

The polymers according to the invention may be prepared on a large industrial scale by known continuous or discontinuous processes.

The polymers according to the invention can be utilised in a broad field of applications. If they are used, for example, as absorbents in sanitary towels, nappies or wound coverings, they have the property of rapidly absorbing large quantities of menstrual blood, urine or other body fluids. Because the agents according to the invention also retain the absorbed liquids at pressure and are additionally able in the swollen state to distribute further liquid within the construction, they are preferably utilized at concentrations, in relation to the hydrophilic fiber material such as, for example, fluff, which are higher than has hitherto been possible. They are also suitable for use as a homogeneous superabsorber layer without a fluff content within nappy construction, as a result of which particularly thin nappies are possible. The polymers are furthermore suitable for use in hygiene articles (incontinence products) for adults.

Such absorbent hygiene products usually have a general structure comprising a liquid-permeable cover (1) facing the body, a liquid-absorbing soaking-up ply (2) as well as a substantially liquid-impermeable outer layer (3) remote from the body. Other constructions for the rapid absorption and distribution of body fluid (4) are also used in the soaking-up core as an option. These constructions are frequently but not necessarily utilized between the liquid-permeable cover (1) facing the body and the liquid-absorbing soaking-up ply (2).

The liquid-permeable cover (1) generally comprises a non-woven fibrous formed fabric or a different porous construction. Synthetic polymers such as, for instance, polyvinyl chloride or polyvinyl fluoride, polytetrafluoroethylene (PTFE), polyvinyl alcohols and derivatives, polyacrylates, polyamides, polyesters, polyurethanes, polystyrene, polysiloxanes or polyolefines (for example polyethylene (PE) or polypropylene (PP)), for example, as well as natural fiber materials as well as any combinations of the aforementioned materials within the meaning of mixed materials or composite materials or copolymers, are considered as materials for this cover (1).

The liquid-permeable cover (1) has a hydrophilic character. It may moreover comprise a combination of hydrophilic and hydrophobic constituents. It is generally preferred to equip the liquid-permeable cover (1) to be hydrophilic, in order to make possible rapid body fluid infiltration times into the liquid-absorbing soaking-up ply (2), however partially hydrophobised covers (1) are also used.

The liquid-absorbing soaking-up ply (2) contains the superabsorbent powder or grains and optionally further components comprising, for example, fibrous materials, foam materials, film-forming materials or porous materials as well as combinations of two or more of these materials. Each of these materials may be of either natural or synthetic origin or may have been prepared by chemical or physical modification of natural materials. The materials may be hydrophilic or hydrophobic, with hydrophilic materials being preferred. This is true in particular of compositions such as are intended for the efficient absorption of discharged body fluids and transport them towards regions of the absorbing core which are more remote from the entry point of the body fluid.

Cellulose fibers, modified cellulose fibers (for example reinforced cellulose fibers), polyester fibers (for example Dacron), hydrophilic nylon or alternatively hydrophilised hydrophobic fibers such as, for example polyolefines (PE, PP), polyesters, polyacrylates, polyamides, polystyrene, polyurethanes and others, which have been hydrophilised with surface-active agents, are, for example, suitable as hydrophilic fiber materials.

Cellulose fibers and modified cellulose fibers are preferably utilized. Combinations of cellulose fibers and/or modified cellulose fibers with synthetic fibers such as, for example, PE/PP composite materials, so-called bicomponent fibers such as are used, for example, for thermobonding of airlaid materials or other materials are likewise common. The fiber materials may be present in various forms for application, for example as cellulose fibers discharged or deposited loose from an air current or aqueous phase, as non-woven formed fabric or as tissue. Combinations of various forms for application are possible.

As an option, further pulverulent substances may be utilized in addition to the superabsorbent polymers according to the invention, such as, for example, deodorising substances such as cyclodextrins, zeolites, inorganic or organic salts and similar materials.

Polymer foams may, for example, be utilized as porous materials and foam materials, such as are described in patent specifications DE 44 18 319 A1 and DE 195 05 709 A1.

Thermoplastic fibers (for example bicomponent fibers prepared from polyolefines), polyolefine grains, latex dispersions or hot-melt adhesives may be used to mechanically stabilize the liquid-absorbing soaking-up ply (2). As an option one or more plies of tissue are used for the purpose of stabilization.

The liquid-absorbing soaking-up ply (2) may be single-ply or may comprise a plurality of layers. Constructions may be used for the purpose which consist of hydrophilic fibers, preferably cellulose fibers, as an option of a construction for the rapid absorption and distribution of body fluid (4), such as, for example, chemically reinforced (modified) cellulose fibers or high-loft formed fabrics prepared from hydrophilic or hydrophilised fibers as well as of superabsorbent polymers.

The superabsorbent polymers according to the invention may here be distributed homogeneously in the cellulose fibers or the reinforced cellulose fibers, they may also be placed in the manner of a ply between the cellulose fibers or the reinforced cellulose fibers, or the superabsorbent polymers may have a concentration gradient within the cellulose fibers or reinforced cellulose fibers. The ratio of the total quantity of superabsorbent polymer to the total quantity of cellulose fibers or the reinforced cellulose fibers in the absorbent soaking-up core may vary between 0 and 100 wt. %, wherein in one embodiment concentrations of up to 100% superabsorbent polymers are possible locally, for example when the charge is gradient-wise or layer-wise. Such constructions having regions of high concentrations of absorbent polymers, with the polymer content in certain regions being between 60 and 100 wt. %, preferably between 90 and 100 wt. %, are also described in the patent specification U.S. Pat. No. 5,669,894, for example.

As an option, a plurality of different superabsorbent polymers which differ, for example, in the soaking-up rate, permeability, storage capacity, absorption opposing pressure, particle distribution, or also chemical composition, may also be utilized concurrently. The different superabsorbers may be placed, mixed with one another, into the soaking-up pad, or alternatively they may be positioned in the absorbent core in locally differentiated manner. Such a differentiated positioning may be effected following the direction of the thickness of the soaking-up pad or the length or width of the soaking-up pad.

There is/are in the liquid-absorbing soaking-up ply (2) one or more plies containing the superabsorbent polymers according to the invention, optionally with cellulose fibers or reinforced cellulose fibers. In a preferred embodiment constructions comprising combinations of plies having a homogeneous superabsorber charge and additionally layer-wise placement are used.

Optionally, the absorption articles may have further plies of pure cellulose fibers or reinforced cellulose fibers on the side facing the body and/or also on the side remote from the body.

The structural possibilities described above can also be repeated in multiple manner, which may be a case of superimposed layering of two or more identical plies or alternatively superimposed layering of two or more different constructions of different structure. In this case the differences are in turn of a purely constructive nature, or alternatively they may reside in the type of material used, such as, for example, the use of absorbent polymers according to the invention or with other polymers but of different cellulose types.

Optionally, the entire soaking-up pad or alternatively individual plies of the liquid-absorbing soaking-up ply (2) may be separated from other components of the absorption article by plies of tissue or they may be in direct contact with other plies or components.

By way of example the construction for the rapid absorption and distribution of body fluid (4) and the liquid-absorbing soaking-up ply (2) may, for example, be separated from one another by tissue or they may alternatively be in direct contact with one another. Where no separate construction for the rapid absorption and distribution of body fluid (4) exists between the liquid-absorbing soaking-up ply (2) and the liquid-permeable cover (1) facing the body, the intent being, rather, to achieve the effect of distribution of liquid by the use of, for example, a specific liquid-permeable cover (1) facing the body, the liquid-absorbing soaking-up ply (2) may likewise as an option be separated by a tissue from the liquid-permeable cover (1) facing the body.

As an option, non-woven formed fabric may also be placed in the liquid-absorbing soaking-up ply (2) in place of tissue. Both components lead to the desired side-effect of stabilising and strengthening the absorption core in the moist state.

The liquid-absorbing soaking-up ply, in particular fiber-containing, superabsorbent polymer-containing, liquid-distributing and liquid-storing layers, can be created by a large number of production processes.

In addition to those established conventional processes which may be summarized under drum-forming with the aid of forming drums, forming pockets and product forms and correspondingly adapted raw materials dispensing devices, modern established processes such as the airlaid process (for example EP 850 615, column 4, line 39 to column 5, line 29, U.S. Pat. No. 4,640,810) with all forms of dispensing, deposition of the fibers and reinforcement such as hydrogen bonding (for example DE 197 50 890, column 1, line 45 to column 3, line 50, thermobonding, latex bonding (for example EP 850 615, column 8, line 33 to column 9, line 17 and hybrid bonding, the wetlaid process (for example PCT WO 99/49905, column 4, line 14 to column 7, line 16), carding, melt-blown and spun-blown processes as well as similar processes for the production of superabsorber-containing non-wovens (within the meaning of the definition of EDANA, Brussels), also in combinations of these processes with and among one another, are to be understood as normal methods for the production of the aforesaid liquid storing means.

The production of laminates within the broadest meaning as well as of extruded and coextruded, wet- and dry- as well as post-reinforced structures are considered as further production processes.

A combination of these production possibilities with and among one another is likewise possible.

Chemically reinforced (modified) cellulose fibers or high-loft formed fabrics prepared from hydrophilic or hydrophilised fibers or a combination of both, for example, may additionally be co-used for the production of absorption articles having rapid absorption and distribution of body fluid (4).

Chemically reinforced, modified cellulose fibers can, for example, be created from cellulose fibers which are reacted by cross-linking agents such as, for example, $C_2$-$C_8$ dialdehydes, $C_2$-$C_8$ monoaldehydes having an additional acid function or $C_2$-$C_9$ polycarboxylic acids in a chemical reaction. Specific examples are: glutaric aldehyde, glyoxal, glyoxalic acid or citric acid. Cationically modified starch or polyamide-epichlorohydrin resins (for example KYMENE 557H, Hercules Inc., Wilmington, Del.) are likewise known. A twisted, crimped structure is achieved and stabilized by cross-linking, which has an advantageous effect on the rate of liquid absorption.

The absorbent hygiene products may vary markedly in their basis weight and thickness, and hence density. Typically, the densities of the regions of the absorption cores are between 0.08 and 0.25 g/cm$^3$. The basis weights are between 10 and 1000 g/m$^2$, with basis weights of between 100 and 600 g/m$^2$ being preferably achieved (see also U.S. Pat. No. 5,669,894). The density generally varies over the length of the absorbing core. This occurs as a consequence of a targeted dispensing of the quantity of cellulose fiber or reinforced cellulose fiber or the quantity of the superabsorbent polymer, because in preferred embodiments these components are placed in greater concentration in the fore region of the absorbing disposable article.

The polymers according to the invention are also utilized in absorber articles which are suitable for additional uses. For these purposes they are processed to form a web, by mixing with paper or fluff or synthetic fibers or by distribution of the superabsorbent polymers between substrates of paper, fluff or non-woven textiles or by processing in carrier materials. Furthermore, the polymers according to the invention also have applications wherever aqueous liquids must be absorbed, such as, for example, in the case of cable sheaths, in food packs, in the agricultural sector in plant cultivation and as water storage means as well as carriers of active substances having a delayed release of the active substance to the environment.

The superabsorbers according to the invention surprisingly show a significant improvement in permeability, that is to say an improvement in the transport of liquid in the swollen state. Polymers having permeability values (SFCs) of up to 70·10$^{-7}$ cm$^3$ s/g at a retention (TB) of at least 27 g/g are obtained, preferably polymers having SFC values of from at least 70·10$^{-7}$ to at least 150·10$^{-7}$ cm$^3$ sec/g at a retention (TB) of at least 25 g/g. Apart from these excellent SFC and retention values, the polymers according to the invention show measured values of at least 18 g/g for liquid absorption at pressure (AAP 0.7 psi).

The products according to the invention having this outstanding property combination of very high SFC values, high retention and high absorption at pressure can be prepared without the use of substances which give cause for toxicological concern.

Testing Methods

In order to characterise the absorbent polymers according to the invention, the retention (TB), absorption at pressure (AAP) and permeability to a 0.9% common salt solution in the swollen state (SFC) are determined.

a) The retention is indicated by the teabag method and is an average value of three measurements. Approximately 200 mg of polymer are welded into a teabag and immersed in 0.9% NaCl solution for 30 minutes. The teabag is then centrifuged in a centrifuge (23 cm diameter, 1,400 rpm) for 3 minutes, and weighed. A teabag containing no water-absorbing polymer is also run as a blank value.

Retention=Amount weighed out−blank value/ Amount weighed in [g/g]

b) Liquid absorption at pressure (AAP test, according to EP 0 339 461).

The absorption at pressure (pressure load 50 g/cm$^2$) is determined by a method described in EP 0 339 461, p. 7. Approximatley 0.9 g superabsorber is weighed into a cylinder with a sieve plate. The uniformly scattered superabsorber layer is placed under load in the form of a plunger exerting a pressure of 50 g/cm$^2$. The pre-weighed cylinder is then placed on a glass filter disk standing in a bowl containing 0.9% NaCl solution, the liquid level of which corresponds precisely to the height of the filter disk. After the cylinder unit has been left to soak up 0.9% NaCl solution for 1 hour, this is re-weighed, and the AAP is calculated as follows:

AAP=amount weighed out(cylinder unit+superabsorber)−amount weighed in (cylinder unit+superabsorber soaked to capacity)/amount of superabsorber weighed in.

c) Permeability in the swollen state (SFC test, according to WO 95/22356). Approximately 0.9 g superabsorber material is weighed into a cylinder having a sieve plate and is distributed carefully on the surface of the sieve. The superabsorber material is allowed to swell for 1 hour against an opposing pressure of 20 g/cm$^2$ in JAYCO synthetic urine [composition: 2.0 g potassium chloride; 2.0 g sodium sulfate; 0.85 g ammonium dihydrogen phosphate; 0.15 g ammonium hydrogen phosphate; 0.19 g calcium chloride; 0.23 g magnesium chloride as anhydrous salts dissolved in 1 litre distilled water]. After determining the swollen height of the superabsorber, 0.118 M NaCl solution are run through the swollen gel layer from a levelled supply vessel at constant hydrostatic pressure. The swollen gel layer is covered during measurement with a special sieve cylinder which guarantees a uniform distribution of the 0.118 M NaCl solution above the gel and constant conditions (measuring temperature 20-25° C.) during measurement in relation to the gel bed state. The pressure acting on the swollen superabsorber continues at 20 g/cm$^2$. With the aid of a computer and scales the quantity of liquid which passes through the gel layer as a function of time is determined at 20-second intervals within a period of 10 minutes. Using regression analysis, the flow rate, g/s, through the swollen gel layer at t=0 is determined at the mid-point of the flow quantity between minutes 2 and 10 by extrapolation of the gradient. The SFC value (K) is calculated as follows:

$$K = \frac{F_s(t=0) \cdot L_0}{r \cdot A \cdot \Delta P} = \frac{F_s(t=0) \cdot L_0}{139506}$$

wherein: $F_s(t=0)$ flow rate in g/s
$L_0$ is the thickness of the gel layer, in cm
r is the density of the NaCl solution (1.003 g/cm$^3$)
A is the area of the upper surface of the gel layer in the measuring cylinder (28.27 cm$^2$)
$\Delta P$ is the hydrostatic pressure bearing on the gel layer (4920 dyne/cm$^2$)
and K is the SFC value [cm$^3$*s*g$^{-1}$].

The formal addition of the numerical values of the teabag retention and the SFC value highlights the abrupt rise in this property combination in the case of the polymers according to the invention, by comparison with untreated superabsorber powder or products post-cross-linked on the surface by known methods. In the case of the products according to the invention the numerical value is not obtained by a high contribution made by one of the two values (for example a high TB retention value and a low SFC value, and vice versa).

EXAMPLES

In the Examples and Comparison Examples the powder utilised in each case for the post-cross-linking surface treatment was screened to a particle size of from 150 μm to 850 μm.

Example 1

1.05 g polyethylene glycol-300 diacrylate and 1.35 g polyethylene glycol(750) monoallyl ether acrylate are dissolved as cross-linking agents in 965.115 g of an aqueous solution of sodium acrylate having a 70 mol % degree of neutralisation (monomer concentration: 37.7%). The monomer solution is purged through with nitrogen for 30 minutes in a plastic polymerisation vessel in order to remove the dissolved oxygen. At a temperature of 4° C. the polymerisation is initiated by the sequential addition of 0.3 g sodium peroxydisulfate in 10 g distilled water, 0.1 g 2,2'-azobis-2-amidinopropane dihydrochloride in 10 g distilled water, 0.07 g 35% hydrogen peroxide solution in 10 g distilled water and 0.015 g ascorbic acid in 2 g distilled water. After the end temperature (approx. 100° C.) had been reached, the gel was comminuted in a mincer and was dried at 150° C. in a circulating air oven for 2 hours. The dried product was broken coarsely, ground, and the particles 150-850 μm in size were segregated for further reaction (powder A).

50 g powder A were mixed, with vigorous stirring, with a solution of 0.25 g aluminium sulfate, 18 hydrate and 0.25 g water and then with a solution of 0.5 g 1,3-dioxolan-2-one and 0.5 g water, and the mixture was then heated in an oven temperature-controlled to 170° C., for 60 minutes.

For the comparison, 50 g powder A were mixed with a solution of 0.5 g 1,3-dioxolan-2-one and 1.25 g water, and the mixture was then heated in an oven temperature-controlled to 170° C., for 60 minutes (Comparison Example 1).

| Product | TB [g/g] | $AAP_{0.7}$ [g/g] | SFC [$cm^3s\ 10^{-7}/g$] | TB + SFC |
|---|---|---|---|---|
| Powder A | 31.0 | | 0 | 31.0 |
| Example 1 | 28.5 | 23.8 | 70 | 98.5 |
| Comparison Example 1 | 28.7 | 25.0 | 20 | 48.7 |

Example 2

50 g powder A were mixed, with vigorous stirring, with a solution of 0.14 g aluminium nitrate, 9 hydrate and 0.14 g water and then with a solution of 0.5 g 1,3-dioxolan-2-one and 0.5 g water, and the mixture was then heated in an oven temperature-controlled to 170° C., for 60 minutes.

For the comparison, 50 g powder A were mixed with a solution of 0.5 g 1,3-dioxolan-2-one and 1.25 g water, and the mixture was then heated in an oven temperature-controlled to 170° C., for 60 minutes (Comparison Example 1).

| Product | TB [g/g] | $AAP_{0.7}$ [g/g] | SFC [$cm^3s\ 10^{-7}/g$] | TB + SFC |
|---|---|---|---|---|
| Powder A | 31.0 | | 0 | 31.0 |
| Example 2 | 28.5 | 24.5 | 75 | 103.5 |

Example 3

0.84 g triallylamine and 1.5 g polyethylene glycol(750) monoallyl ether acrylate are dissolved as cross-linking agents in 965.175 g of an aqueous solution of sodium acrylate having a degree of neutralisation of 70 mol % (monomer concentration: 37.7%). The monomer solution is purged with nitrogen for 30 minutes in a plastic polymerisation vessel in order to remove the dissolved oxygen. At a temperature of 4° C. the polymerisation is initiated by the sequential addition of 0.3 g sodium peroxydisulfate in 10 g distilled water, 0.1 g 2,2'-azobis-2-amidinopropane dihydrochloride in 10 g distilled water, 0.07 g 35% hydrogen peroxide solution in 10 g distilled water and 0.015 g ascorbic acid in 2 g distilled water. After the end temperature (approx. 100° C.) had been reached, the gel was comminuted in a mincer and was dried at 150° C. in a circulating air oven for 2 hours. The dried product was broken coarsely, ground, and the particles 150-850 μm in size were segregated for further reaction (powder B).

50 g powder B were mixed, with vigorous stirring, with a solution of 0.25 g aluminium sulfate, 18 hydrate, 0.5 g hydroxymethyl-1,3-dioxolan-2-one and 1.25 g water and the mixture was then heated in an oven temperature-controlled to 180° C., for 30 minutes (Example 3).

50 g powder B were mixed, with vigorous stirring, with a solution of 0.5 g 1,3-dioxolan-2-one, 0.05 g ethylene glycol diglycidyl ether and 1.5 g water, and the mixture was then heated in an oven temperature-controlled to 180° C., for 30 minutes (Comparison Example 2).

50 g powder B were mixed, with vigorous stirring, with a solution of 0.25 g glycerol, 0.25 g 1,3-dioxolan-2-one and 1.5 g water, and the mixture was then heated in an oven temperature-controlled to 180° C., for 30 minutes (Comparison Example 3).

50 g powder B were mixed, with vigorous stirring, with a solution of 0.25 g 1,3-dioxolan-2-one, 0.25 g ethylenediamine and 1.5 g water and then heated in an oven temperature-controlled to 180° C., for 30 minutes (Comparison Example 4).

| Product | TB [g/g] | $AAP_{0.7}$ [g/g] | SFC [$cm^3s\ 10^{-7}/g$] | TB + SFC |
|---|---|---|---|---|
| Powder B | 30.5 | | 0 | 30.5 |
| Example 3 | 26.0 | 22.7 | 65 | 91 |
| Comparison Example 2 | 26.7 | 23.4 | 37 | 63.7 |
| Comparison Example 3 | 26.4 | 22.8 | 42 | 68.4 |
| Comparison Example 4 | 26.8 | 20.6 | 16 | 42.8 |

What is claimed:

1. A pulverulent polymer which absorbs water, aqueous or serous liquids as well as blood, which is post-cross-linked on the surface and is synthesized from
   a) from about 55 to about 99.9 wt. % polymerized, ethylenically unsaturated, acid group-containing monomers which are at least about 25 mol % neutralized,
   b) from 0 to about 40 wt. % polymerized, ethylenically unsaturated monomers which are copolymerizable with a),
   c) from about 0.1 to about 5.0 wt. % of one or more polymerized cross-linking agents,
   d) from 0 to about 30 wt. % of a water-soluble polymer, wherein the sum of the quantities by weight a) to d) is 100 wt. %, wherein the polymer is formed into polymer particles that are coated and post-cross-linked, with heating, with e) from about 0.01 to about 5 wt. %, in relation to the polymer, of an organic surface post-cross-linking agent, with the exception of polyols, in the form of an aqueous solution and with f) from about 0.001 to about 1.0 wt. %, in relation to the polymer, of a trivalent or a higher-valent cation in the form of a salt dissolved in an aqueous solution, g) the polymer particles coated with elements e) and f) are heat treated at a temperature from at least 150 to 250° C. to form the pulverulent polymer, and wherein the total quantity of water of the coating solution is from about 0.5 to about 10 wt %, in relation to the polymer, and the ratio by weight of the salt to the post-cross-linking agent is within the range from about 1:0.8 to about 1:4 wherein the pulverulent polymer has a retention (TB) of at least about 25 g/g and a saline flow permeability (SFC) of about $45 \times 10^{-7}$ cm$^3$sec/g or more.

2. The pulverulent polymer according to claim 1 wherein the ratio by weight of water-soluble salt to the post-cross-linking agent is from about 1:1 to about 1:3.5.

3. The pulverulent polymer according to claim 1 wherein the component e) has been utilized at from about 0.1 to about 2.5 wt. %, and the component f) has been utilized at from about 0.005 to about 0.5 wt. %.

4. The pulverulent polymer according to claim 1 wherein only water has been utilized as a solvent for the components e) and f).

5. The pulverulent polymer according to claim 1 wherein the components e) and f) have been utilized together in an aqueous solution.

6. The pulverulent polymer according to claim 1 wherein the total quantity of water of the aqueous solutions which are added separately or together was from about 0.75 to about 5 wt. %.

7. The pulverulent polymer according to claim 1 wherein the component f) is a cation of iron, aluminum, titanium or of a further transition metal, or of a double salt of two different cations or of a mixture of the salts.

8. The pulverulent polymer according to claim 1 wherein the organic surface post crosslinking agent is an alkylene carbonate.

9. The pulverulent polymer according to claim 6 wherein the alkylene carbonate 1,3-dioxolan-2-one has been utilized, and as the salt an inorganic aluminum salt has been utilized.

10. The pulverulent polymer according to claim 1 wherein at least about 50% of the acid groups of the monomer units a) are carboxyl groups.

11. The pulverulent polymer according to claim 1 wherein the monomer units a) are derived from acrylic acid and/or methacrylic acid.

12. The pulverulent polymer according to claim 1 wherein the component d) is selected from the group consisting of starch, polyvinyl alcohol and derivatives thereof.

13. The pulverulent polymer according to claim 1 wherein the polymer has a retention (TB) of at least about 27 g/g at a permeability (SFC) of up to about $70 \cdot 10^{-7}$ cm$^3$sec/g.

14. The pulverulent polymer according to claim 1 wherein the polymer has a permeability (SFC) of from at least about $70 \cdot 10^{-7}$ to about $150 \cdot 10^{-7}$ cm$^3$sec/g.

15. The pulverulent polymer according to claim 13 wherein the polymer has a liquid absorption at pressure (AAP) at 0.7 psi of at least about 18 g/g.

16. A process for the preparation of absorbent polymers according to claim 1 wherein a mixture of:

a) from about 55 to about 99.9 wt. % ethylenically unsaturated, acid group-carrying monomers which are at least about 25 mol % neutralized, b) from 0 to about 40 wt. % ethylenically unsaturated monomers which are copolymerizable with a), c) from about 0.1 to about 5.0 wt. % of one or more cross-linking compounds, d) from 0 to about 30 wt. % of a water-soluble polymer, wherein the sum of the components a) to d) is 100 wt. %, is radically polymerized, optionally comminuted, dried, pulverized, sieved, and then the resulting pulverized polymer powder is treated with e) from about 0.01 to about 5 wt. %, in relation to the polymer, of an organic surface post-cross-linking agent, with the exception of polyols, in the form of an aqueous solution and with f) from about 0.005 to about 0.5 wt. %, in relation to the polymer, of a trivalent or a higher-valent cation of a salt dissolved in an aqueous solution, g) the polymer particles coated with elements e) and f) are heat treated at a temperature from at least 150 to 250° C. to form the pulverulent polymer, and wherein the salt and the surface post-cross-linking agent are utilized in a ratio by weight of from about 1:0.8 to about 1:4 and the total quantity of water of the aqueous coating solution(s) is from about 0.5 to about 10 wt. %, in relation to the polymer, and wherein, with intensive mixing of the aqueous solutions of the components e) and f) which are present together or separately, with the polymer powder and with heating, a post-cross-linking of the polymer powder takes place.

17. The process according to claim 16 wherein the polymer powder utilized has a moisture content of from about 0.5 to about 25 wt. %.

18. The process according to claim 16 wherein the polymer powder utilized has a particle size of less than about 3000 μm.

19. The process according to claim 16 wherein the aqueous solutions of the components e) and f) are heated up to from about 20° C. to about 100° C. before they are utilized.

20. Absorption agents for water, aqueous liquids or blood, foamed and non-foamed flat materials, in packaging materials, in constructions for plant cultivation, as carriers for soil improvers or as carriers for active substances comprising pulverulent polymer made according to claim 1.

21. A predominant to sole absorption agent in at least one layer of absorbent inserts comprising the pulverulent polymer made according to claim 1.

22. A pulverulent polymer which absorbs water, aqueous or serous liquids as well as blood, which is post-cross-linked on the surface and the pulverulent polymer consists essentially of a) from about 55 to about 99.9 wt. % polymerized, ethylenically unsaturated, acid group-containing monomers which are at least about 25 mol % neutralized, b) from 0 to about 40 wt. % polymerized, ethylenically unsaturated monomers which are copolymerizable with a), c) from about 0.1 to about 5.0 wt. % of one or more polymerized cross-linking agents, d) from 0 to about 30 wt. % of a water-soluble polymer, wherein the sum of the quantities by weight a) to d) is 100 wt. %, wherein the polymer is formed into polymer particles that are coated and post-cross-linked, with heating, with e) from about 0.01 to about 5 wt. %, in relation to the polymer, of an organic surface post-cross-linking agent, with the exception of polyols, in the form of an aqueous solution and with
f) from about 0.001 to about 1.0 wt. %, in relation to the polymer, of a trivalent or a higher-valent cation in the form of a salt dissolved in an aqueous solution,
g) the polymer particles coated with elements e) and f) are heat treated at a temperature from at least 150 to 250° C. to form the pulverulent polymer, and wherein the total quantity of water of the coating solution is from about 0.5 to about 10 wt. %, in relation to the polymer, and the ratio by weight of the salt to the post-cross-linking agent is within the range from about 1:0.8 to about 1:4 wherein the pulverulent polymer has a retention (TB) of at least about 25 g/g and a saline flow permeability (SFC) of about $45 \times 10^{-7}$ cm$^3$sec/g or more.

* * * * *

UNITED STATES PATENT AND TRADEMARK OFFICE
CERTIFICATE OF CORRECTION

PATENT NO. : 7,285,599 B2 Page 1 of 1
APPLICATION NO. : 10/379827
DATED : October 23, 2007
INVENTOR(S) : Richard Mertens and Jörg Harren It is certified that error appears in the above-identified patent and that said Letters Patent is hereby corrected as shown below:

Title page:

Item [75],
"Harren Jörg" should read --Jörg Harren--.

Signed and Sealed this

First Day of July, 2008

JON W. DUDAS
*Director of the United States Patent and Trademark Office*